United States Patent
Ng et al.

(10) Patent No.: US 9,839,748 B2
(45) Date of Patent: Dec. 12, 2017

(54) IV FLOW REGULATOR

(71) Applicant: Becton Dickinson Holdings Pte Ltd, Singapore (SG)

(72) Inventors: Mum Pew Ng, Singapore (SG); Jithendra Kumar, Singapore (SG); Darius Alisantoso, Singapore (SG)

(73) Assignee: Becton Dickinson Holdings Pte. Ltd., Singapore (SG)

( * ) Notice: Subject to any disclaimer, the term of this patent is extended or adjusted under 35 U.S.C. 154(b) by 61 days.

(21) Appl. No.: 14/837,843

(22) Filed: Aug. 27, 2015

(65) Prior Publication Data
US 2016/0106913 A1    Apr. 21, 2016

(30) Foreign Application Priority Data

Oct. 20, 2014    (CN) .................... 2014 2 0607256 U

(51) Int. Cl.
| | |
|---|---|
| *A61M 5/168* | (2006.01) |
| *A61M 5/162* | (2006.01) |
| *A61M 39/10* | (2006.01) |
| *F16K 5/04* | (2006.01) |

(Continued)

(52) U.S. Cl.
CPC ........ *A61M 5/16804* (2013.01); *A61M 5/162* (2013.01); *A61M 5/16822* (2013.01); *A61M 5/16877* (2013.01); *A61M 39/1011* (2013.01); *F16K 5/0407* (2013.01); *A61M 5/1413* (2013.01); *A61M 5/16881* (2013.01); *A61M 2039/1033* (2013.01); *A61M 2205/3334* (2013.01); *A61M 2205/582* (2013.01); *A61M 2206/20* (2013.01); *F16K 5/10* (2013.01)

(58) Field of Classification Search
CPC .......... A61M 5/16804; A61M 5/16813; A61M 5/16822; A61M 5/162; A61M 5/16877; F16K 5/10; Y10T 137/87925–137/87973; Y10T 137/9029
See application file for complete search history.

(56) References Cited

U.S. PATENT DOCUMENTS

| | | |
|---|---|---|
| 3,880,401 A | 4/1975 | Wiltse |
| 4,471,942 A | 9/1984 | Kocanowski |
| 6,156,025 A | 12/2000 | Niedospial, Jr. et al. |

(Continued)

FOREIGN PATENT DOCUMENTS

| | | |
|---|---|---|
| WO | 8600682 A1 | 1/1986 |
| WO | 2014116998 A2 | 7/2014 |
| WO | 2015073603 A1 | 5/2015 |

OTHER PUBLICATIONS

Foreign Communication From a Related Counterpart Application, European Search Report dated Mar. 21, 2016, EP Application No. 15181776.4, 9 pages.

*Primary Examiner* — Nathan R Price
*Assistant Examiner* — Courtney Fredrickson

(57) ABSTRACT

There is provided an IV flow regulator including a first part integrated with a flow control slit, the flow control slit being along a fluid path; a second part integrated with a central stem, the central stem including a spiral surface configured to contact the flow control slit, an area of contact defined by the spiral surface and the flow control slit being shaped substantially like an orifice to enable flow along the fluid path; and a dead space chamfer included in the second part at a portion of the fluid path subsequent to the area of contact.

13 Claims, 8 Drawing Sheets

(51) Int. Cl.
F16K 5/10 (2006.01)
A61M 5/14 (2006.01)

(56) References Cited

U.S. PATENT DOCUMENTS 7,361,165 B2 * 4/2008 Simon ............... A61M 5/16804
                                                      604/246
2010/0013215 A1  1/2010 Werth

* cited by examiner

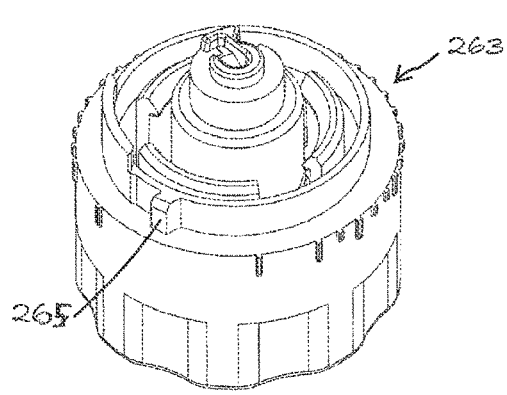
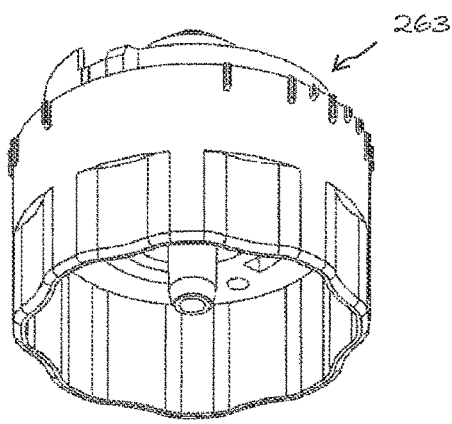
Figure 12(a)
Figure 12(b)
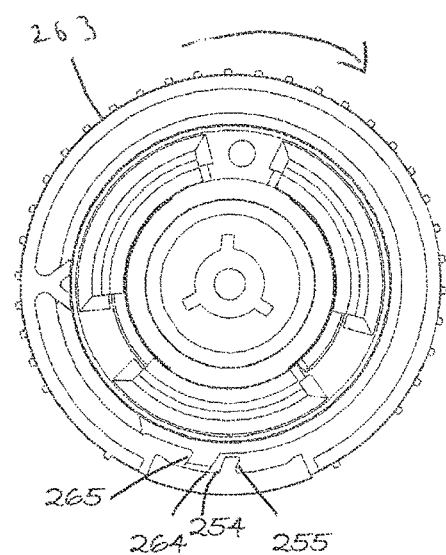
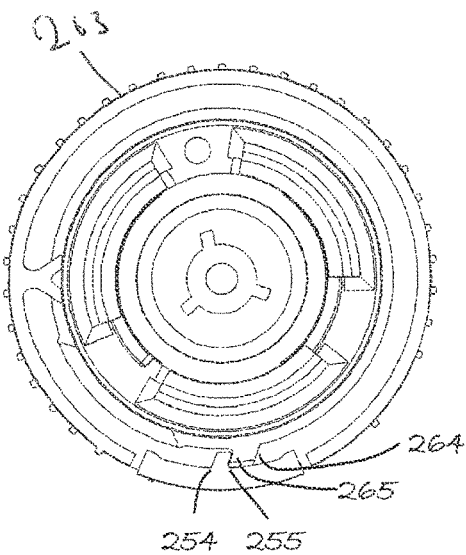
Figure 13(a)
Figure 13(b)

IV FLOW REGULATOR

CROSS-REFERENCE TO RELATED APPLICATIONS

This application claims priority to Chinese Application No. CN 2014020607256.4 filed with the Intellectual Property Office of China on Oct. 20, 2014 and entitled "IV FLOW REGULATOR," which is incorporated herein by reference in its entirety for all purposes.

FIELD OF INVENTION

The invention generally relates to an intravenous (IV) flow regulator.

BACKGROUND

IV sets currently in the market typically uses a roller clamp or flow regulator to control flow rate. The use of a roller clamp is an economical way (only two plastic parts) of regulating flow rate by restricting a cross sectional area of the IV tube (by using roller and cam path from housing to pinch or release the tube). Unfortunately, it is time consuming for clinicians to set a desired flow rate because there are no markings on a roller clamp housing, and flow rate consistency changes over time due to the reaction forces from the IV tube to the roller clamp assembly.

However, even though flow regulators with dial markings have been used for clinicians to quickly set desired and more consistent flow rates, there are shortfalls with the use of known flow regulators as well. Since current flow regulators do not interact with tubes and typically function by diverting fluid flow into the flow regulator, unfortunately, this leads to a high tendency for leakage, as well as sterility issues. As such, current flow regulators typically have additional parts (such as elastomers) to provide seals which overcome the aforementioned issues. Consequently, this causes the cost of the flow regulator to be higher than the roller clamp due to use of more parts and a more expensive manufacturing process to assemble the higher number of parts.

In addition, the use of either the roller clamp or the flow regulator leads to a common problem of tampering with the roller clamp or the flow regulator by third parties. This could be fatal and at the very least, it results in incorrect dosage of the IV solution.

Even though there are flow regulators in the market which do provide a locking feature for a desired flow rate selected by clinicians, the locking feature is typically enabled with use of an additional part to carry out this locking function. This is typically an active lock that requires a user to lock/unlock before carrying out other functions such as flow rate selection. This clearly increases operation complexity, materials cost and manufacturing costs.

It is thus appreciated that there are issues with existing flow regulators in the market.

SUMMARY

There is provided an IV flow regulator including a first part integrated with a flow control slit, the flow control slit being along a fluid path; a second part integrated with a central stem, the central stem including a spiral surface configured to contact the flow control slit, an area of contact defined by the spiral surface and the flow control slit being shaped substantially like an orifice to enable flow along the fluid path; and a dead space chamfer included in the second part at a portion of the fluid path subsequent to the area of contact.

The IV flow regulator can further include an interlocking sheath with at least one stopper structure integrated with the first part; and a snap-fit structure integrated with the second part. It is preferable that the at least one stopper structure couples with the snap-fit structure. It is also preferable that the snap-fit structure is subject to a pre-tension force and that the interlocking sheath is configured to couple with the central stem to provide a hermetic seal.

It is advantageous that the dead space chamfer is configured to prevent entrapment of air in fluids passing through the IV flow regulator.

The IV flow regulator may further include a plurality of indicators and a reference indicator, with the plurality of indicators being spaced apart in an adjacent configuration.

The IV flow regulator may further include a gear rack integral with either the first part or the second part; and a locking lever integral with the part without the gear rack. It is advantageous that the at least one tooth of the locking lever is configured to be engaged with the gear rack. Advantageously, engagement of the at least one tooth in the gear rack is configured to provide a tactile feedback.

Alternatively, the IV flow regulator may further include a protrusion including a reverse angled face integral with either the first part or the second part; and a locking lever integral with the part without the protrusion. It is advantageous that a rib of the locking lever is configured to be engaged with the protrusion. Advantageously, engagement of the rib with the protrusion is configured to provide a tactile feedback.

It is preferable that the locking lever is centrally pivoted and configured to be in a biased state. The IV flow regulator may further include an IV tube holder integrated with the first part.

Advantageously, any point along the fluid path other than the area of contact is configured to have a cross sectional area of greater than 1.7 mm$^2$.

DESCRIPTION OF FIGURES

In order that the present invention may be fully understood and readily put into practical effect, there shall now be described by way of non-limitative example only preferred embodiments of the present invention, the description being with reference to the accompanying illustrative figures.

FIG. 12(a) shows a top perspective view and FIG. 12(b) shows a bottom perspective view of a lower component of the third embodiment.

FIG. 13(a) shows a cross-sectional view of the third embodiment in an unlocked configuration and FIG. 13(b) shows a locked configuration.

DESCRIPTION OF PREFERRED EMBODIMENTS

Figure 1:
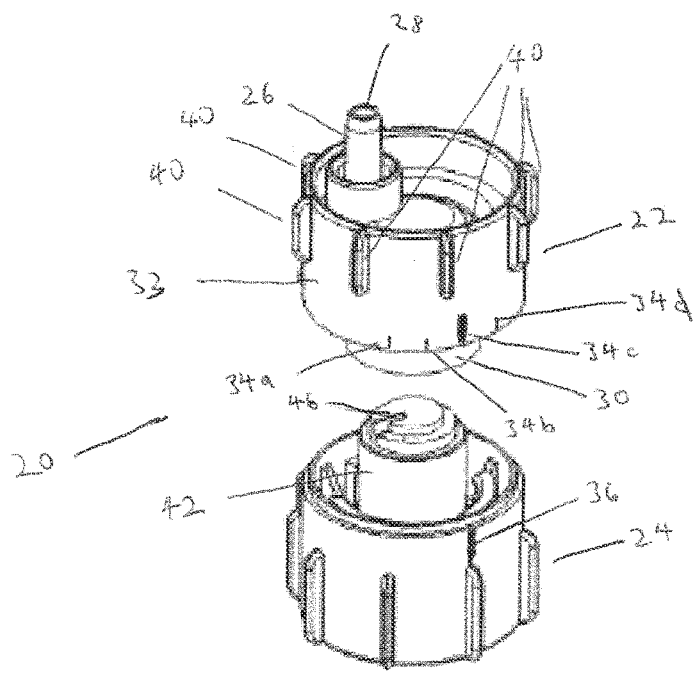
FIG. 1 shows an exploded perspective view of a first embodiment of the present invention.
Figure 2:
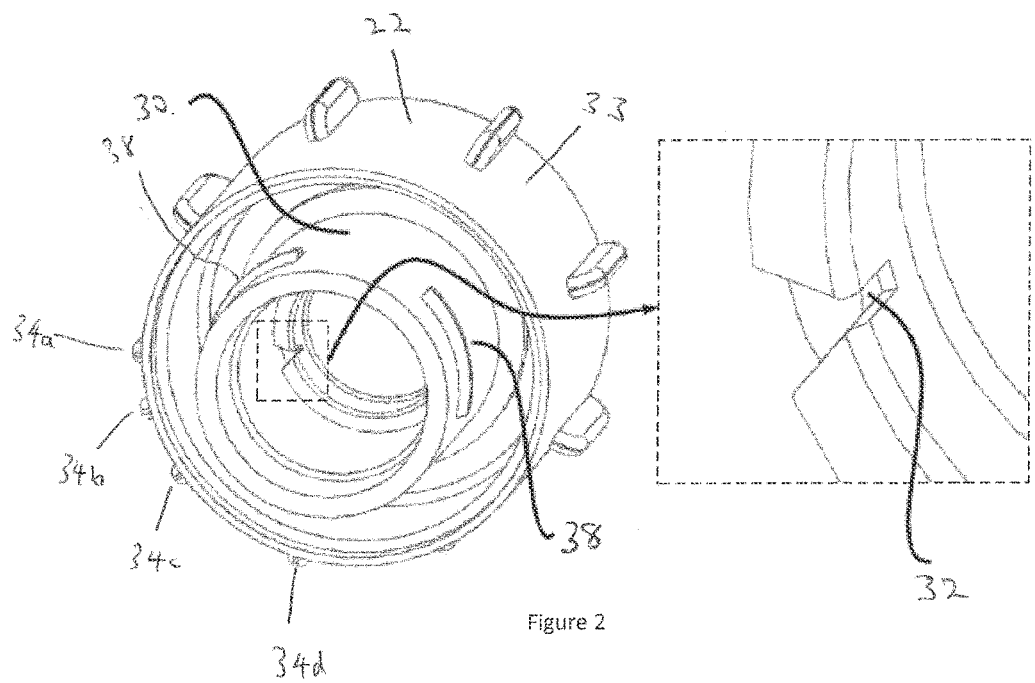
FIG. 2 shows a perspective view of a first portion of the first embodiment of FIG. 1.
Figure 3:
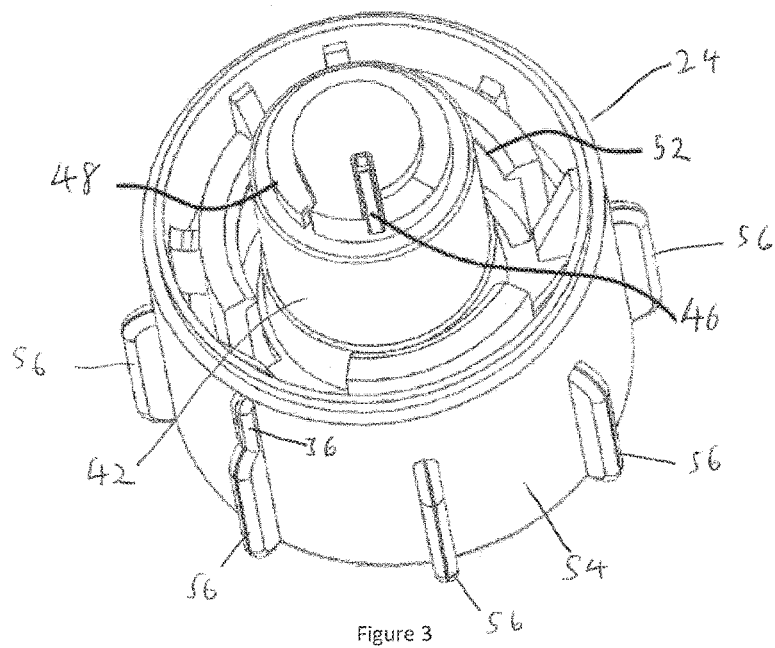
FIG. 3 shows a perspective view of a second portion of the first embodiment of FIG. 1.

The present invention provides an IV flow regulator with only two discrete parts, and also includes a locking feature to prevent tampering of the IV flow regulator by third parties. In this regard, the present invention provides an IV flow regulator with an anti-tampering feature and which is fabricated in a low cost manner because there are only two discrete parts. The present invention will also bring about other benefits, as will be evident from the subsequent paragraphs.

Referring to FIGS. 1 to 4, there is shown a first embodiment of the present invention of an IV flow regulator 20. The IV flow regulator 20 comprises a first part 22 and a second part 24. The IV flow regulator 20 provides a fluid path arrangement which takes manufacturing processes (such as, for example, parts assembly, molding tooling constructions and so forth) into consideration, to achieve a two portion construction that is able to operate in a desired manner. The first part 22 and the second part 24 are both fabricated from a plastic material.

The first part 22 includes a spout 26, the spout 26 including an inlet channel 28. The spout 26 is configured to couple with an IV tube during use of the IV flow regulator 20. The first part 22 also includes an interlocking sheath 30 which is configured to guide the first part 22 to mount to the second part 24. The interlocking sheath 30 includes a flow control slit 32 which is configured to restrict a flow of fluid passing through the IV flow regulator 20, and also includes at least one stopper structure 38 configured to engage with the second part 24 when the first part 22 is mounted to the second part 24.

A holding surface 33 of the first part 22 includes a plurality of indicators 34a, 34b, 34c, 34d. The plurality of indicators 34a, 34b, 34c, 34d are used together with a reference indicator 36 on the second part 24 to indicate of flow rate of fluid passing through the IV flow regulator 20. The plurality of indicators 34a, 34b, 34c, 34d can be either physical markers (embossed as shown or recessed) or printed markers. In the first embodiment, when first indicator 34d is aligned with the reference indicator 36, it indicates that there is no fluid flow through the IV flow regulator 20. When second indicator 34c is aligned with the reference indicator 36, it indicates a first fluid flow rate through the IV flow regulator 20. When third indicator 34b is aligned with the reference indicator 36, it indicates a second fluid flow rate through the IV flow regulator 20. When fourth indicator 34a is aligned with the reference indicator 36, it indicates a third fluid flow rate through the IV flow regulator 20. It is noted that the third fluid flow rate is greater than the second fluid flow rate, and the second fluid flow rate is greater than the first fluid flow rate. Other than the plurality of indicators 34a, 34b, 34c, 34d, the holding surface 33 also includes a plurality of ribs 40 to aid a user when gripping the holding surface 33.

Figure 14:
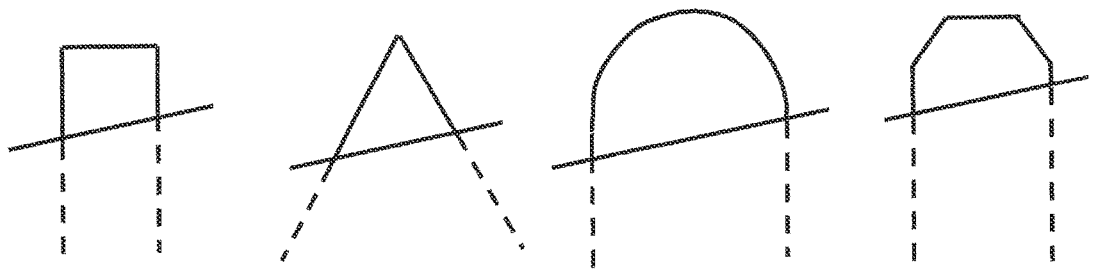
FIG. 14 shows example shapes of a flow control area of the present invention.

The second part 24 includes a central stem 42, whereby the central stem 42 includes an outlet 44 for fluid flowing through the IV flow regulator 20. The central stem 42 is configured to guide the interlocking sheath 30 to enable the first part 22 to mount to the second part 24. The central stem 42 also includes an exit passage 46 configured for redirecting fluid flow. In addition, a flow control edge 48 of the central stem 42 is a spiral surface which contacts the flow control slit 32 of the first part 22, where an area of contact is known as a flow control area 50. It should be appreciated that the flow control area 50 is shaped substantially like an orifice. Sample shapes of the orifice, such as, for example, trapezoidal, triangular, semi-elliptical and polygonal are depicted in FIG. 14. It should be appreciated that it is a cross sectional area (sufficiently small to restrict fluid flow) of the orifice which controls fluid flow, and not the shape of the orifice. Thus, it should be appreciated that the formation of the orifice does not require a precise positioning between the flow control slit 32 and the flow control edge 48. Fluid flow rate depends on a position of the flow control area 50 in relation with the flow control slit 32. It is appreciated that any point along the fluid path in the IV flow regulator 20 other than the flow control area 50 is configured to have a cross sectional area of greater than 1.7 mm$^2$. The second part 24 also includes a snap-fit structure 52 adjacent to the central stem 42, the snap-fit structure 52 being configured for coupling with the at least one stopper structure 38 of the first part 22. Moreover, a gripping surface 54 includes a plurality of ribs 56 to aid a user when gripping the gripping surface 54.

It should be noted that the first part 22 and the second part 24 are formed by injection moulding. The exit passage 46 configured to redirect fluids is made using core-cavity tooling construction.

The operation of the IV flow regulator 20 will now be described in greater detail in the following paragraphs.

Flow Regulation

Figure 4:
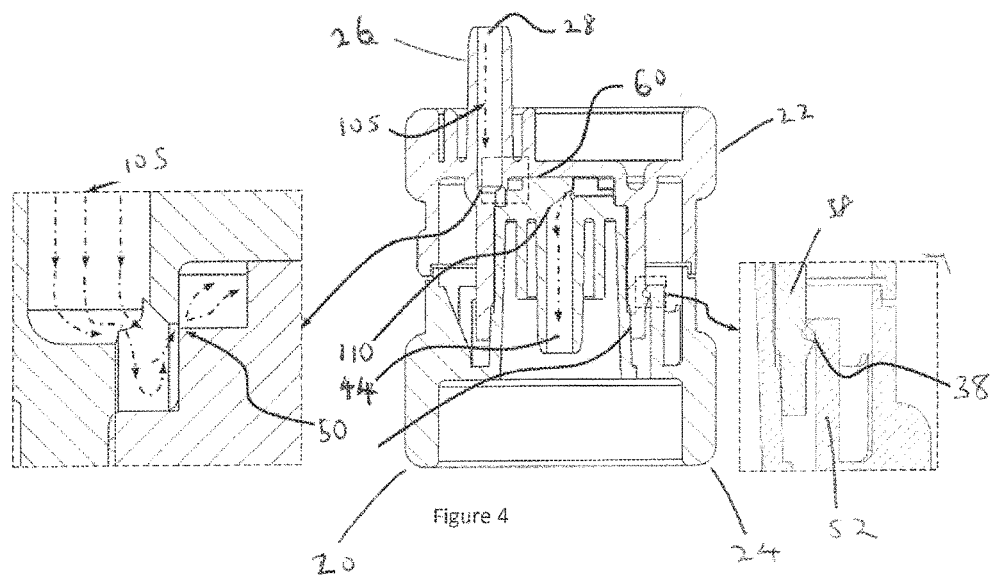
FIG. 4 shows a cross-sectional view of the first embodiment of FIG. 1.
Figures 5A, 5B:
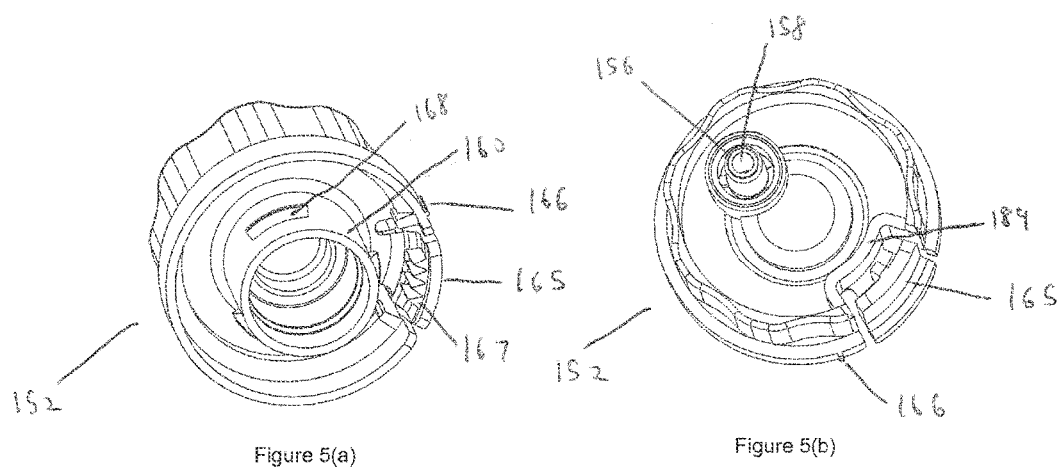
FIG. 5(a) shows a top perspective view and FIG. 5(b) shows a bottom perspective view of a top component of a second embodiment of the present invention.
Figure 6:
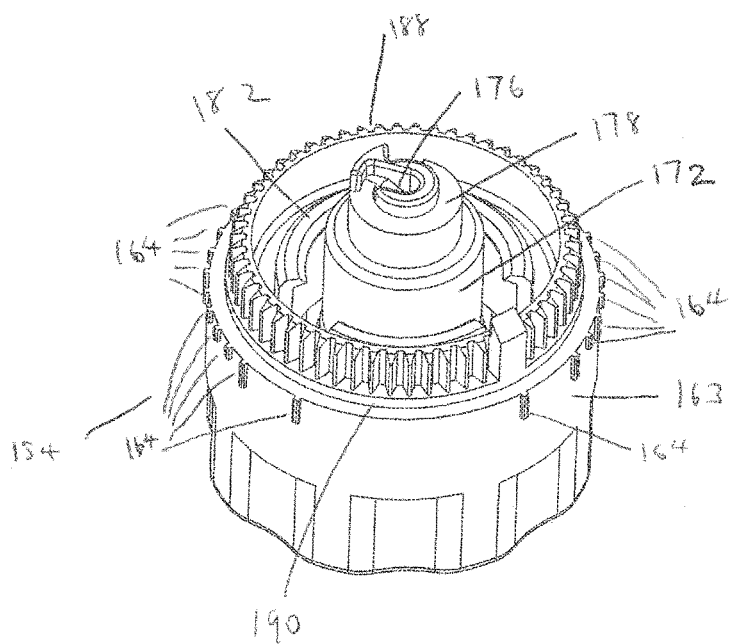
FIG. 6 shows a perspective view of a bottom component of a second embodiment of the present invention.
Figure 9:
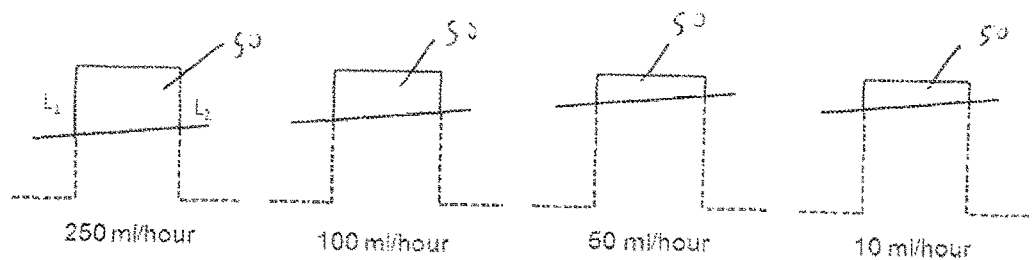
FIG. 9 shows a representation of a flow rate variation of the first and second embodiments.
Figure 10:
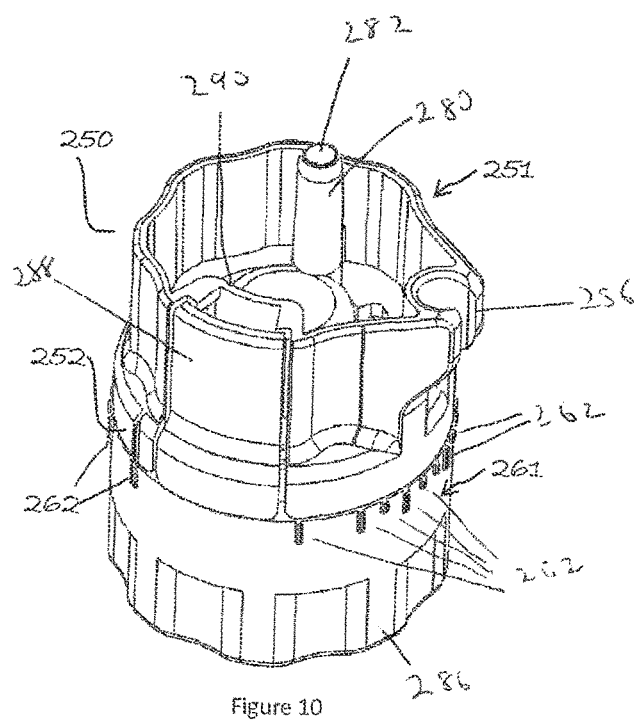
FIG. 10 shows a perspective view of a third embodiment of the present invention.
Figure 11A:
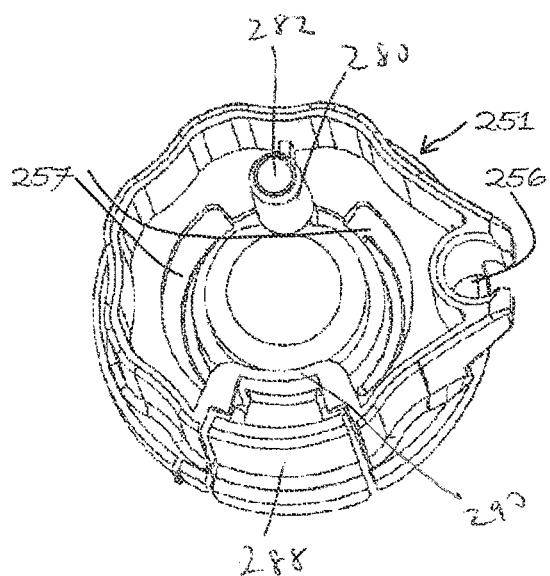
FIG. 11(a) shows a top perspective view and FIG. 11(b) shows a bottom perspective view of an upper component of the third embodiment.
Figure 11B:
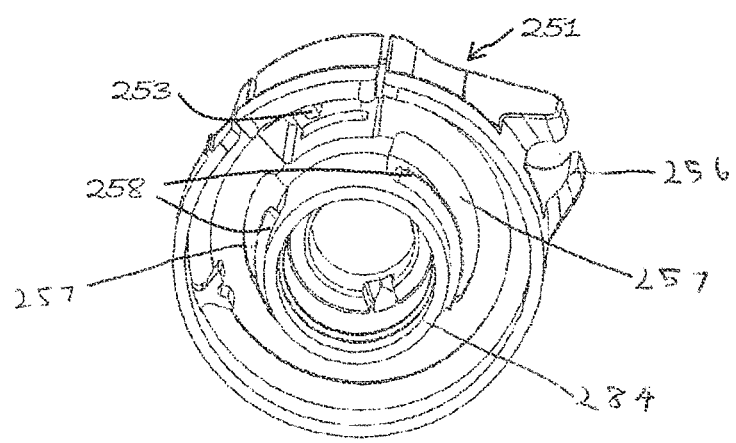

Referring to FIG. 4, dotted lines indicate fluid flow 105 in the IV flow regulator 20. The flow control edge 48 of the central stem 42 is a spiral surface which contacts the flow control slit 32 of the first part 22, correspondingly forming a flow control area 50. The flow control area 50 is defined by the spiral surface and the flow control slit 32. It should be appreciated that the flow control area 50 is shaped substantially like an orifice. Fluid flow rate depends on a position of the flow control area 50 in relation with the flow control slit 32. This change in position of the flow control area 50 will result in a smaller or larger opening of the flow control slit 32. Referring to FIG. 9, it should be noted that the larger the flow control area 50, the greater the rate of flow. Thus, flow regulation in the IV flow regulator 20 is achieved. The shape of the flow control area 50 is substantially shaped like an orifice as an orifice is able to control flow more consistently and is less sensitive to pressure changes. This is in accordance with Bernoulli's equation, as follows:

$$Q = C_B \sqrt{(\Delta P / \rho)} \qquad (1)$$

Where:
  Q=Flow rate
  ΔP=Pressure drop
  ρ=Density of fluid
  $C_B$=Numerical constant depending on geometrical configuration of the orifice The following assumptions are made for equation (1), namely:

The fluid is incompressible.

Friction by viscous forces is negligible.

Thus, as the shape of the flow control area 50 is substantially shaped like an orifice, fluid flow in the IV flow regulator 20 is more consistent as it is less sensitive to pressure changes as shown in equation (1).

Dimensional Control

In order to ensure that dimensions and fit of the flow control area 50 does not change, the snap-fit structure 52 and the at least one stopper structure 38 couple with one another after assembly and thus creates a resultant force biasing the first part 22 towards a datum 60 on the central stem 42. The resultant force is due to a pre-tension shape design of the snap-fit structure 52 (with slanted surfaces that always pushes the first part 22 to bias towards the datum 60 after assembly). Such a configuration eliminates assembly misfits between the first part 22 and the second part 24. This ensures that there is flow rate accuracy in the IV flow regulator 20. With the use of the pre-tension shape design of the snap-fit structure 52, the need for assembly clearance required for typical snap-fit couplings has been eliminated.

Non-Leakage

When assembling the IV flow regulator 20, the interlocking sheath 30 of the first part 22 will couple with the central stem 42 of the second part 24 to form an interference fit that can achieve a hermetic seal without using other parts to enable a sealing function.

Flow Rate Indicators

The IV flow regulator 20 provides the plurality of indicators 34a, 34b, 34c, 34d for indicating a flow rate of fluid passing through the IV flow regulator 20. The plurality of indicators 34a, 34b, 34c, 34d are used together with the reference indicator 36 to indicate the flow rate of the fluid. Thus, given that the plurality of indicators 34a, 34b, 34c, 34d and the reference indicator 36 are integrated with the IV flow regulator 20, thus, there is no need for another separate part for dial markings to indicate the flow rate of the fluid. It should be appreciated that the plurality of indicators 34a, 34b, 34c, 34d can be on the second part 24 and the reference indicator 36 can be on the first part 22.

Minimisation of Air Entrapment in Fluids

When the exit passage 46 is aligned with the datum 60, the fluid passing through the IV flow regulator 20 will exit through the outlet 44. This eliminates dead space along the fluid path. A dead space chamfer 110 is included in the second part 24 at a portion of the fluid path after the flow control area 50 to further prevent air entrapment in the fluid.

Fast Occlude Mode

During the process of priming an IV line (that is, filling the IV line with infusate), it is desirable if a duration when switching from a fluid flow mode to a no flow (occlude) mode on a flow regulator is minimised so as to minimise wastage of fluid. In the IV flow regulator 20, location of the first indicator 34d and the second indicator 34c in adjacent positions enable fast change from fluid flow mode to occlude mode.

Referring to FIGS. 5 to 8, there is shown a second embodiment of the present invention of an IV flow regulator 150. The IV flow regulator 150 comprises a top component 152 and a base component 154. The IV flow regulator 150 provides a fluid path arrangement which takes manufacturing processes (such as, for example, parts assembly, molding tooling constructions and so forth) into consideration, to achieve a two portion construction that is able to operate in a desired manner. The top component 152 and the base component 154 are both fabricated from a plastic material.

The top component 152 includes a spout 156, the spout 156 including an inlet channel 158. The spout 156 is configured to couple with an IV tube during use of the IV flow regulator 150. The top component 152 also includes an interlocking sheath 160 which is configured to guide the top component 152 to mount to the base component 154. The interlocking sheath 160 includes a flow control slit (not shown) which is configured to restrict a flow of fluid passing through the IV flow regulator 150, and also includes at least one stopper structure 168 configured to engage with the base component 154 when the top component 152 is mounted to the base component 154.

A holding surface 163 of the base component 154 includes a plurality of indicators 164. The plurality of indicators 164 are used together with a reference indicator 166 on the top component 152 to indicate a flow rate of fluid passing through the IV flow regulator 150, in a similar manner to the first embodiment. The plurality of indicators 164 can be either physical markers (embossed as shown or recessed) or printed markers. The top component 152 also includes a locking lever 165, the locking lever 165 including at least one tooth 167 configured to engage with a gear rack. The locking lever 165 can include more teeth 167 if it is thicker in width. The top component 152 also includes a stopper structure 189.

The base component 154 includes a central stem 172, whereby the central stem 172 includes an outlet 174 for fluid flowing through the IV flow regulator 150. The central stem 172 is configured to guide the interlocking sheath 160 to enable the top component 152 to mount to the base component 154. The central stem 172 also includes an exit passage 176 configured for redirecting fluid flow. In addition, a flow control edge 178 of the central stem 172 is a spiral surface which contacts the flow control slit of the top component 152, where an area of contact is known as a flow control area. It is appreciated that any point along the fluid path in the IV flow regulator 150 other than the flow control area is configured to have a cross sectional area of greater than 1.7 mm$^2$. It should be appreciated that the flow control aspect of IV flow regulator 150 is substantially similar to that of IV flow regulator 20. The base component 154 also includes a snap-fit structure 182 adjacent to the central stem 42, the snap-fit structure 182 being configured for coupling with the at least one stopper structure 168 of the top component 152. The base component 154 also includes a gear rack 188 located at a top edge 190 of the base component 154. The at least one tooth 167 of the locking lever 165 engages with the gear rack 188 to prevent rotation of the top component 152 relative to the base component 154 and vice versa.

Figure 7:
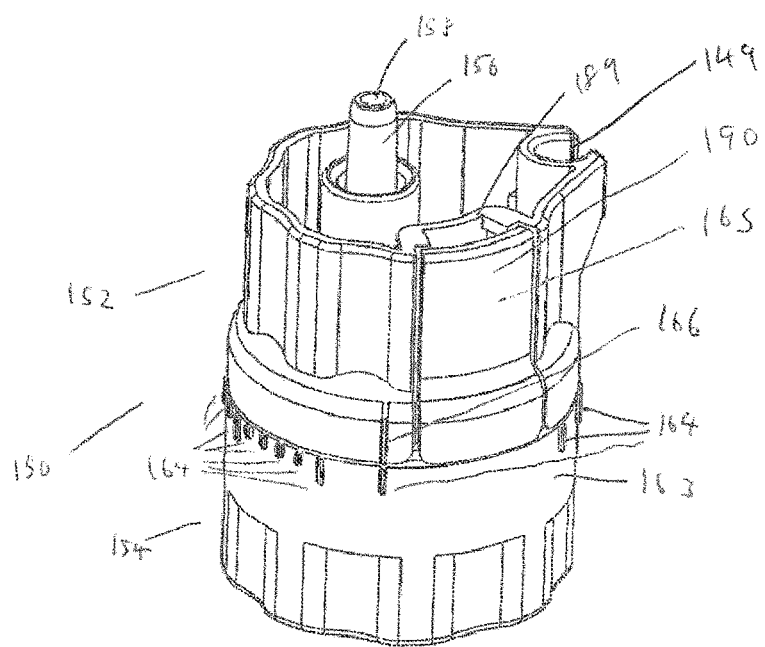
FIG. 7 shows a perspective view of the second embodiment of the present invention.
Figure 8:
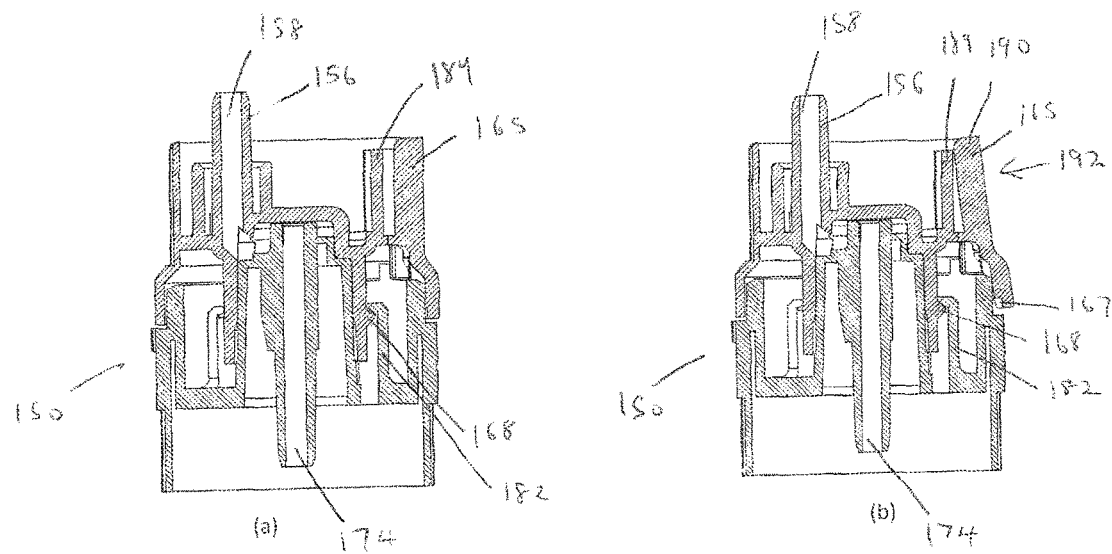
FIG. 8 shows a cross-sectional view of the second embodiment when undergoing locking.

It should be noted that the top component 152 and the base component 154 are formed by injection moulding. The exit passage 176 configured to redirect fluids is made using core-cavity tooling construction. It should be appreciated that the IV flow regulator 150 is nearly identical to the IV flow regulator 20 except for the additional features of the locking lever 165, the stopper structure 189 and the gear rack 188. FIG. 7 shows the top component 152 with an IV tube holder 149. The IV tube holder 149 is not shown in FIG. 5 as the IV tube holder 149 can be an optional feature on the top component 152. The IV tube holder 149 can be molded out together by simple tooling construction without the use of complicated sliders or lifters. The IV tube holder 149 allows a user to be able to hold IV tubing where a distal tip of the IV tubing (not shown) can be located during initial setup or priming of the IV line. This prevents contamination of the distal tip of the IV tubing which is typically connected to devices such as another IV line or an IV catheter.

Referring to FIG. 8(a), the IV flow regulator 150 is in a locked mode to prevent tampering of the flow rate. FIG. 6(b) shows the IV flow regulator 150 is in an unlocked mode, whereby a user applies a force 192 at an upper portion 190 of the locking lever 165 to actuate the upper portion 190 towards the spout 156. This causes the at least one tooth 167 to be displaced from an existing position at the gear rack 188 as the locking lever 165 is centrally pivoted. Consequently, this allows the top component 152, to move relative to the base component 154. Once the force 192 is removed, the biased nature of the locking lever 165 causes movement of the at least one tooth 167. If the at least one tooth 167 is fully engaged at the gear rack 188, the IV flow regulator 150 then returns to the locked mode of FIG. 6(a). However, if removal of the force 192 leads to semi-engagement of the at least one tooth 167 with the gear rack 188, this means that a twisting motion (regardless of clockwise or anti-clockwise) will need to be applied to the top component 152 to enable the at least one tooth 167 to be fully engaged with the gear rack 188. It should be noted that the locking lever 165 could also be integral with the base component 154, and the gear rack 188 could be integral with the top component 152.

It should be appreciated that the IV flow regulator 150 provides additional advantages over IV flow regulator 20 such as, for example:

Providing a locking effect (passive lock) after flow rate selection has been completed by a user. This will reduce occurrences of tampering with a desired flow rate setting. The locking feature in IV flow regulator 150 is easy to use for the user and yet is designed in a manner which is not evident for an IV recipient to tamper with the flow rate setting. This anti-tampering aspect ensures recipient safety and medicine dosage accuracy.

Providing a one-step process of flow rate selection and automatic lock. This is convenient for the user.

Providing a robust IV flow regulator as the locking lever 165 is the sole moving part of the top component 152, and the stopper structure 189 is configured to prevent over-pressing of the locking lever 165. Moreover, creep failure during release of the locking lever 165 is minimised.

Providing a tactile feedback in relation to each flow rate setting by using an appropriate gear rack 188 to receive the at least one tooth 167.

Referring to FIGS. 10 to 13, there is shown a third embodiment of the present invention of an IV flow regulator 250. The IV flow regulator 250 is similar to the IV flow regulator 150, with the main difference pertaining to a mechanism to cause the IV flow regulator 250 to be in a locked mode.

The IV flow regulator 250 comprises an upper component 251 and a lower component 261. The IV flow regulator 250 provides a fluid path arrangement which takes manufacturing processes (such as, for example, parts assembly, molding tooling construction and so forth) into consideration, to achieve a two portion construction that is able to operate in a desired manner. The upper component 251 and lower component 261 are both fabricated from a plastic material.

The upper component 251 includes a spout 280, the spout 280 including an inlet channel 282. The spout 280 is configured to couple with an IV tube during use of the IV flow regulator 250. The upper component 251 also includes an interlocking sheath 284 which is configured to guide the upper component 251 to mount to the lower component 261. The interlocking sheath 284 includes a flow control slit (not shown) which is configured to restrict a flow of fluid passing through the IV flow regulator 250, and also includes at least one stopper structure 258 configured to engage with the lower component 261 when the upper component 251 is mounted to the lower component 261. The upper component 251 also includes a stopper structure 290. It is appreciated that any point along the fluid path in the IV flow regulator 250 other than a flow control area (where the flow control slit is located) is configured to have a cross sectional area of greater than 1.7 mm$^2$.

A holding surface 286 of the lower component 261 includes a plurality of indicators 262. The plurality of indicators 262 are used together with a reference indicator 252 on the upper component 251 to indicate a flow rate of fluid passing through the IV flow regulator 250, in a similar manner to the second embodiment. The plurality of indicators 262 can be either physical markers (embossed as shown or recessed) or printed markers. The upper component 251 also includes a centrally pivoted and biased locking lever 288, the locking lever 288 including a rib 253 configured to engage with a protrusion 265 (with a reverse angled face) so as to prevent relative movement between the upper component 251 and lower component 261.

The rib 253 and the protrusion 265 are configured to engage with each other in a manner whereby the rib 253 is disengaged easily when the upper component 251 is rotated clockwise relative to the lower component 261 (as shown in FIG. 13(a)). However, once the rib 253 is engaged with the protrusion 265, the IV flow regulator 250 is in a locked mode, and an anti-clockwise rotation of the upper component 251 is not possible unless the locking lever 288 is actuated to disengage the rib 253 from the protrusion 265. This allows the user to quickly proceed to flow regulation after initial setup of the IV set where the IV flow regulator 250 is at an unlocked mode. Thus, the IV flow regulator 250 can be configured to provide a tactile feedback and prevent accidental tampering that will cause over-dosage of medication to a patient.

The upper component 251 includes an IV tube holder 256 which is molded out together by simple tooling construction without the use of complicated sliders or lifters. The IV tube holder 256 allows a user to be able to hold IV tubing where a distal tip of the IV tubing (not shown) can be located during initial setup or priming of the IV line. This prevents contamination of the distal tip of the IV tubing which is typically connected to devices such as another IV line or an IV catheter.

Compared to the second embodiment, a tooling complexity to form a snap-fit feature 258 that is integrated together with the upper component 251 has been simplified by use of an opening 257 which allows simple core-cavity construction without having complicated sliders or lifters. This also reduces parts variation and cost of manufacturing by simplifying tooling construction and maintenance. In addition to this benefit, it should be appreciated that the third embodiment also enables the same advantages as the second embodiment.

Whilst there have been described in the foregoing description preferred embodiments of the present invention, it will be understood by those skilled in the technology concerned that many variations or modifications in details of design or construction may be made without departing from the present invention.

The invention claimed is:

1. An IV flow regulator including:
   a first part integrated with a flow control slit configured to restrict a flow of fluid passing through the IV flow regulator, the flow control slit being along a fluid path within the IV flow regulator;
   a second part integrated with a central stem, the central stem including a spiral surface configured to contact the flow control slit, an orifice defined by the spiral surface and the flow control slit to enable flow along the fluid path; and
   a dead space chamfer included in the second part at a portion of the fluid path subsequent to the orifice where an exit passage of the central stem joins orthogonally to an outlet of the central stem, wherein the dead space chamfer prevents entrapment of air where fluids pass orthogonally to the outlet through the IV flow regulator.

2. The IV flow regulator of claim 1, further including:
   an interlocking sheath with at least one stopper structure integrated with the first part; and
   a snap-fit structure integrated with the second part,
   wherein the at least one stopper structure couples with the snap-fit structure.

3. The IV flow regulator of claim 2, wherein the snap-fit structure is subject to a pre-tension force.

4. The IV flow regulator of claim 2, wherein the interlocking sheath is configured to couple with the central stem to provide a hermetic seal.

5. The IV flow regulator of claim 1, further including a plurality of indicators and a reference indicator.

6. The IV flow regulator of claim 5, wherein the plurality of indicators are spaced apart in an adjacent configuration.

7. The IV flow regulator of claim 1, further including:
   a gear rack integral with either the first part or the second part; and
   a locking lever integral with the part without the gear rack,
   wherein at least one tooth of the locking lever is configured to be engaged with the gear rack.

8. The IV flow regulator of claim 1, further including:
   a protrusion integral with either the first part or the second part; and
   a locking lever integral with the part without the protrusion,
   wherein a rib of the locking lever is configured to be engaged with the protrusion.

9. The IV flow regulator of claim 8, wherein the locking lever is centrally pivoted and configured to be in a biased state.

10. The IV flow regulator of claim 7, wherein engagement of the at least one tooth in the gear rack is configured to provide a tactile feedback.

11. The IV flow regulator of claim 8, wherein engagement of the rib with the protrusion is configured to provide a tactile feedback.

12. The IV flow regulator of claim 1, further including an IV tube holder integrated with the first part.

13. The IV flow regulator of claim 1, wherein any point along the fluid path other than the orifice is configured to have a cross sectional area of greater than $1.7 \text{ mm}^2$.

* * * * *